US008596129B2

United States Patent
Niese

(10) Patent No.: US 8,596,129 B2
(45) Date of Patent: Dec. 3, 2013

(54) EMUS TRANSDUCER SYSTEM AS WELL AS A METHOD FOR PRODUCING LINEARLY POLARISED TRANSVERSE WAVES WITH VARIABLY PREDETERMINABLE POLARISATION DIRECTION WITHIN A TEST SPECIMEN

(75) Inventor: Frank Niese, Saarbrücken (DE)

(73) Assignee: Fraunhofer-Gesellschaft zur Förderung der Angewandten Forschung E.V., Munich (DE)

( * ) Notice: Subject to any disclaimer, the term of this patent is extended or adjusted under 35 U.S.C. 154(b) by 253 days.

(21) Appl. No.: 13/155,427

(22) Filed: Jun. 8, 2011

(65) Prior Publication Data

US 2011/0296920 A1    Dec. 8, 2011

(30) Foreign Application Priority Data

Jun. 8, 2010    (DE) .......................... 10 2010 023 028

(51) Int. Cl.
*G01N 29/24*    (2006.01)
*G01N 29/00*    (2006.01)

(52) U.S. Cl.
USPC ............................................. 73/643; 73/597

(58) Field of Classification Search
USPC ........... 73/643, 576–578, 620, 622, 624, 632, 73/597–599; 702/38–39
See application file for complete search history.

(56) References Cited

U.S. PATENT DOCUMENTS

| | | | |
|---|---|---|---|
| 4,727,321 A * | 2/1988 | Huschelrath ................... | 324/226 |
| 4,793,185 A * | 12/1988 | Boettger et al. ................. | 73/643 |
| 5,987,993 A * | 11/1999 | Meier et al. ..................... | 73/643 |
| 6,009,756 A * | 1/2000 | Willems et al. .................. | 73/643 |
| 6,347,550 B1 * | 2/2002 | Kroening et al. ............... | 73/598 |
| 6,502,463 B1 * | 1/2003 | Clark et al. ...................... | 73/643 |
| 6,766,694 B2 * | 7/2004 | Hubschen ........................ | 73/643 |
| 7,024,935 B2 * | 4/2006 | Paige et al. ...................... | 73/643 |
| 7,395,715 B2 * | 7/2008 | Salzburger et al. ............. | 73/643 |
| 7,434,467 B2 * | 10/2008 | Hubschen et al. ............... | 73/643 |
| 8,146,431 B2 * | 4/2012 | Yashan et al. ................... | 73/643 |

FOREIGN PATENT DOCUMENTS

DE    41 01 942 A1    8/1991

OTHER PUBLICATIONS

Frank Niese et al: "Wall Thickness Measurement Sensor for Pipeline Inspection using EMAT Technology in Combination with Pulsed Eddy Current and MFL", $9^{th}$ European Confernece on NDT, 2006, Berlin.
B. Igarashi et al: "Excitation of Bulk Shear Waves in Steel by Magnetostricitive Coupling", 1998 IEEE Ultrasonics Symposium Proceedings, pp. 893-896.
M. Hirao and H. Ogi (2003), EMATS for Science and Industry (Kluwer Academic Publishers).

* cited by examiner

*Primary Examiner* — Helen Kwok
(74) *Attorney, Agent, or Firm* — Antonelli, Terry, Stout & Kraus, LLP.

(57) ABSTRACT

An EMUS transducer system for producing linearly polarized transverse waves having a variably predeterminable polarization direction within a test specimen containing at least ferromagnetic material portions and having a test specimen surface, a magnetization unit produces a magnetic field orientated parallel to the test specimen surface within the test specimen. At least one HF coil on the test specimen surface produces or detects a HF field combined with the magnetic field orientated parallel to the test specimen surface within the test specimen. The magnetization unit includes at least three magnetization bodies spatially separated from one another to introduce a magnetic field into the test specimen. The magnetic flux emanating from at least one of magnetization bodies a spatial direction relative to the test specimen surface is varied.

13 Claims, 3 Drawing Sheets

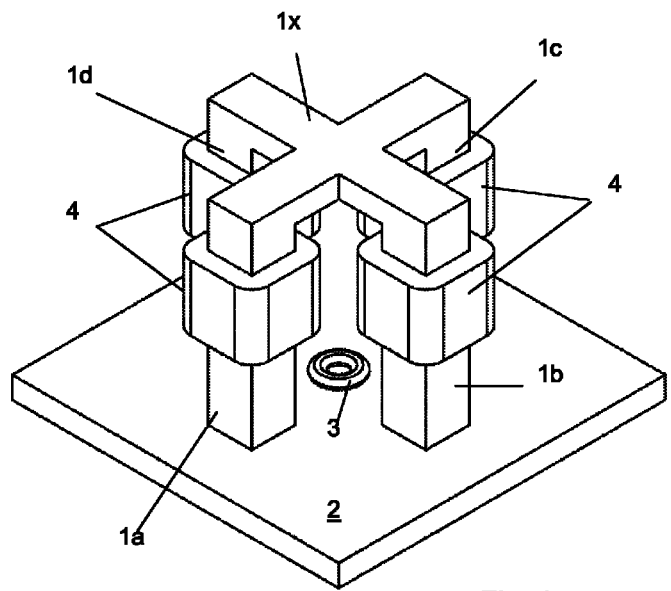
Fig. 1
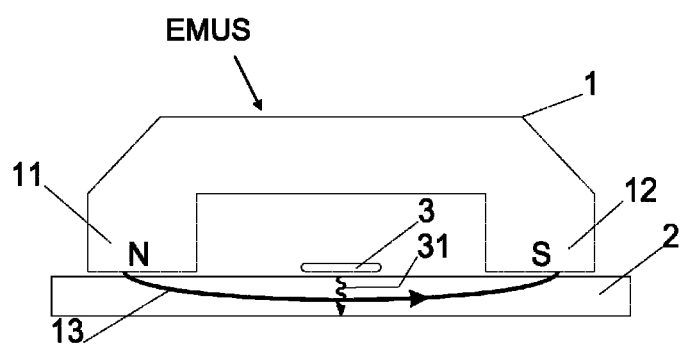
Fig. 2 - PRIOR ART

EMUS TRANSDUCER SYSTEM AS WELL AS A METHOD FOR PRODUCING LINEARLY POLARISED TRANSVERSE WAVES WITH VARIABLY PREDETERMINABLE POLARISATION DIRECTION WITHIN A TEST SPECIMEN

BACKGROUND OF THE INVENTION

1. Field of the Invention

The invention relates to an EMUS transducer system and a method for producing linearly polarized transverse waves with a variably predeterminable polarisation direction within a test specimen containing at least ferromagnetic material portions. A test specimen surface with a magnetization unit provided which is arrangeable on the surface of the test specimen and produces a magnetic field orientated parallel to the test specimen surface within the test specimen. At least one HF coil arrangement is provided and is arrangeable on the test specimen surface and for producing or detecting a HF field overlaid with the magnetic field.

2. Description of the Prior Art

Linearly polarized ultrasound (US) transverse waves are preferably used for non-destructive material testing and also for assessing material states, such as textures or inner stresses. To this end, it is necessary to orientate the polarization direction of the linearly polarized US transverse waves to be coupled into the material to be investigated in each case parallel and perpendicularly to the preferential direction of the respective texture or inner stress, for detecting and correspondingly evaluating propagation differences of the US waves characteristic of anisotropic material in respective propagation directions. In addition, by suitable orientation, that is to say rotation of the polarization direction of the US waves relatively to the material structure, for example workpieces made from cast iron, optimum propagation conditions for US waves can be created, in order to bring about evaluable interactions between the US waves and the respective workpiece. It is also possible to detect the orientation of cracks running perpendicularly to the workpiece surface into the interior of the material in a spatially resolved manner.

Linearly polarized US transverse waves are typically produced by piezoelectric or electromagnetic ultrasound transducers.

The use of piezoelectric ultrasound transducers necessitates the use of a coupling means, providing ultrasound signals or vibrations produced by a piezoelectric ultrasound probe to be coupled into a workpiece to be investigated or out of the same again. However, the coupling means, as well as the coupling gap thickness between the workpiece surface and the ultrasound probe, influence the signal quality and therefore the validity of the measurement results in a disadvantageous manner. Especially in the case of transverse waves, there is furthermore a requirement for a coupling medium, which is as highly-viscous as possible, as a result of which the test conditions are made more difficult, particularly in the case of probe movements. In addition, the coupling means contaminates the workpiece surface which is a circumstance occurring undesirably and in particular in the case of investigations on quality surfaces. Additionally, the use of coupling means limits the use of this investigation method on workpieces at higher temperatures.

An alternative to this result is the use of electromagnetic ultrasound transducers (EMUS), which was transversely polarized ultrasound waves guided in a mode-pure manner which can be excited particularly well. In this technology, ultrasound signals are excited and picked up directly in the layers of a component close to the surface without coupling means, that is to say contactlessly by means of electromagnetic interaction. In ferromagnetic materials, the excitation is mainly based on the effect of magnetostriction, by contrast the Lorentz force acts as the excitation mechanism in non-magnetic, electrically conductive materials. More information on this can be drawn from the following articles: Hirao, M. and Ogi, H. (2003), EMATS for Science and Industry (Kluwer Academic Publishers) and also Igarashi, B., Alers, G. A., "Excitation of Bulk Shear Waves in Steel by Magnetostrictive Coupling", IEEE Ultrasonic Symposium Proceedings (1998) 893-896.

In FIG. 2, a prior art EMUS transducer arrangement is illustrated which produces transversely polarized ultrasound waves within a workpiece 2 made of ferromagnetic material is illustrated. The EMUS transducer has a magnetization unit 1 and also a HF coil system 3. The magnetization unit 1, which can be constructed in the form of a permanent magnet or an electromagnet operated with direct current or low-frequency alternating current, provides two regions 11 and 12 which can be placed onto the test sample surface. One region constitutes the magnetic north pole N and the other region constitutes the magnetic south pole S. In this manner, a magnetic field 13 orientated parallel to the test sample surface is introduced into the test specimen 2. The HF coil system 3, which can be a single coil or of a plurality of coils, is located between the magnetic north and south poles of the magnetization unit 1 as close to the surface as possible on the test specimen surface, in order to produce a modulated high-frequency electromagnetic field 13 which is orientated parallel to the test specimen surface, in the region of the parallel orientated magnetic field 13 within the test specimen 2 by corresponding electrical excitation, preferably by means of a powerful HF burst signal. Due to magnetostrictive effects acting within the ferromagnetic material of the test specimen 2, oscillating forces arise due to the modulation of the quasi-stationary magnetic field 13 by the high-frequency electromagnetic field. These oscillating forces are used as sources for ultrasound signals, particularly in the form of transversely polarized ultrasound waves 31 propagating perpendicularly to the test specimen surface. In the case of reception, the processes are reciprocal to these processes. More details about this can be drawn from the following article: Niese, F., Yashan, A., Wilhelms, H., "Wall Thickness Measurement Sensor for Pipeline Inspection Using EMAT Technology in Combination with Pulsed Eddy Current and Magnetic Flux Leakage", 9th European Conference on NDT, 2006, Berlin.

In order to be able to perform material investigations with an EMUS probe, it is necessary to rotate the entire EMUS probe relative to the test specimen surface, particularly as the polarization direction of a linearly polarized transverse wave 31 created with an EMUS probe of the type of construction illustrated in FIG. 2 is always aligned parallel to the magnetization direction along the parallel running magnetic lines of the magnetic field 13 within the test specimen 2. A rotation at least of the magnetization unit 1 is in many cases connected with additional mechanical outlay which is furthermore undesirable, particularly as the measurement constellation relative to the test object is subject to a change as a result, which is error-prone for an exact investigation of location-dependent material states in test specimens.

A test apparatus for testing ferromagnetic workpieces using ultrasound waves is disclosed in DE 41 01 942, which provides an overlaying of an alternating magnetic field orientated parallel to the workpiece surface with a stationary or quasi-stationary magnetic field orientated perpendicularly to the workpiece surface for the oblique sonic impingement of vertically polarized ultrasound waves into the workpiece to be investigated. A HF coil arrangement for coupling eddy currents into the workpiece is attached in the region of the magnetic field orientated perpendicularly to the workpiece surface. For the direction-selective sonic impingement, high-frequency transmitting pulses are triggered for controlling the HF coil arrangement either in the region of the lower or upper half waves of the alternating current. It is neither possible to create ultrasound waves propagating into the workpiece vertically to the workpiece surface with a test arrangement of this type. Moreover, influence on the spatial orientation of the polarization direction is not provided.

SUMMARY OF THE INVENTION

The invention is an EMUS transducer system and a method for producing linearly polarized transverse waves with variably predeterminable polarization direction within a test specimen containing at least ferromagnetic material portions in such a manner that a mechanical rotation of the test specimen arrangement for purposes of a change of the polarization direction of the ultrasound waves produced within the test specimen is prevented to the greatest extent possible. The goal is to be able to perform measurements on test specimens using linearly polarized transverse waves with variably predeterminable polarization directions, without moving the EMUS transducer system and in particular the magnetization unit relatively to the test specimen.

The EMUS transducer system according to the invention for producing linearly polarized transverse waves with a variably predeterminable direction within a test specimen containing at least ferromagnetic material portions and with a test specimen surface. According to the invention, the magnetization unit has at least three magnetization bodies spatially separated from one another, which are provided and set up to be placeable onto the test specimen surface. In each case, they introduce magnetic field lines with a predeterminable magnetic flux into the test specimen. Further, means are provided, for changing magnetic flux of the magnetic field introduced into the test specimen, which emanate from at least one magnetization body, so that the spatial direction of the magnetic field forming parallel to the test specimen surface within the test specimen can be changed in a predeterminable manner.

In order to be able to perform the rotation of the magnetic field without a mechanical movement of the magnetization unit, the magnetic field within the test specimen, which forms between the magnetic poles of only two magnetization bodies placed on the test specimen surface, is overlaid in a controllable manner by a further magnetic field which is introduced into the test specimen at least by a further magnetization body, so that one resulting magnetic field forms from the at least two magnetic fields. The magnetic field lines of the magnetic field are likewise orientated parallel to the test specimen surface, but with a changed propagation direction, at least within a test specimen region in which the high-frequency electromagnetic field which can be produced for the part of the HF coil system is able to propagate effectively and enters into interaction with the resulting magnetic field. For the controllable overlaying of the individual magnetic fields, the strength of the magnetic flux of the magnetic fields to be introduced into the test specimen can be varied and are located on at least one and preferably on all of the magnetization bodies. In this manner it is possible, to influence the spatial orientation of the magnetic field lines of the magnetic field responsible for producing the linearly polarized transverse waves and therefore also the polarization direction of the transverse waves themselves in a targeted manner exclusively by suitable variation of the magnetic flux strength of the individual magnetic fields contributing to the formation of the resulting magnetic field.

The term "magnetizing body" is here very generally understood to be a corporeally constructed magnet which has at least one freely accessible surface which at the same time corresponds to the region of a magnetic pole. The freely accessible surface is preferably constructed in such a manner that it can be placed onto the test specimen surface over as large an area as is possible. That is to say in a contour fitting manner, in order to enable the magnetic field coupling into the test specimen wither with low losses or free of losses as possible. Fundamentally, it is possible to construct the magnetization bodies separately from one another, for example in the form of bar-shaped magnet bodies.

In a preferred embodiment, the magnetization bodies are in each case connected in pairs to their magnet body regions opposite the freely accessible surfaces in each case via a magnetically effective connecting yoke, in order to strengthen the magnetic flux to be introduced via both magnetization bodies into the test specimen. Two magnetization body pairs connected in this manner are arranged relatively to the test specimen surface so that their magnetically active connecting yokes cross or cross over in projection onto the test specimen surface. A possible embodiment variant provides the connecting yokes in one piece in each case, with construction of a so-called cross yoke so that all magnetization bodies are integrally connected to one another via their respective connecting yokes. Another embodiment variant provides a separate construction of two magnetization body pairs with different overall heights in each case, which enable a spatially separate cross over point with respect to their magnetically active connecting yokes.

For the variation of the magnetic flux of the magnetic fields to be introduced into the test specimen via the magnetization bodies in each case, means for influencing the strength of the magnetic flux are provided at least on one of preferably however on all magnetization bodies. As the further embodiments will show, the means concern the electrically activatable magnetic coils attached to the magnetization bodies in the case of electromagnetically constructed magnetization bodies. In the case of permanent magnetic magnetization bodies, flux-conducting pieces, magnetically interact with the magnetization bodies and are movably arranged.

Although the exemplary embodiments explained in the following are limited to EMUS transducer systems with a magnetization unit, which is constructed on the basis of two magnetization body pairs arranged in a crossed state in each case, it is possible to construct only three or even more than four magnetization bodies alone or in a star-shaped mutual yoke connection. All EMUS transducer systems constructed in accordance with the invention are based on the invention generating a uniform resulting magnetic field with magnetic field lines orientated parallel to the test specimen surface and can be rotated in a controlled manner about an axis orientated perpendicularly to the test specimen surface, by controlled overlaying of at least two controllable magnetic fields.

A method according to the invention based on operating principle for producing ultrasound waves in the form of linearly polarized transverse waves with a variably predeterminable polarization direction consequently stands out in that at least two magnetic fields orientated parallel to the test specimen surface are produced within the test specimen with the magnetic field lines being cut at an angle $\alpha \cdot 0°$, preferably $\alpha=90°$ and in that a change of the magnetic flux of at least one of the two magnetic fields is performed so that a uniform magnetic field orientated parallel to the test specimen surface results with a uniformly predeterminable magnetic field line orientation. The production of the magnetic fields acting in the test specimen can either be realized with the aid of an electromagnet arrangement or a permanent magnet arrangement. In the case of an electromagnet arrangement, the change of the magnetic flux of the at least one magnetic field involved is performed by controlled variation of an electrical supply voltage and/or electrical current feeding the electromagnet arrangement. In the case of the production of the magnetic fields by a permanent magnet arrangement, it is valid for changing the magnetic flux of at least one of the magnetic fields involved to perform a spatial variation of at least one permanent magnet or a magnetic flux-conducting piece. Concrete examples are to be drawn from the exemplary embodiments described in the following. It is also possible to combine both principles for magnetic field production with one another, in that for example a magnetization body pair is composed of two magnetization body pairs made up of permanent magnets arranged in a crossed state in each case and the other magnetization body pair being constructed in the form of an electromagnet arrangement.

BRIEF DESCRIPTION OF THE DRAWINGS

The invention is described by way of example in the following without limitation of the general inventive idea on the basis of exemplary embodiments with reference to the drawings. In the drawings:

FIG. 1 shows an EMUS transducer system in the form of an electromagnet arrangement having a one-piece cross yoke;

FIG. 2 shows a prior art EMUS transducer;

DETAILED DESCRIPTION OF THE INVENTION

Figure 3A:
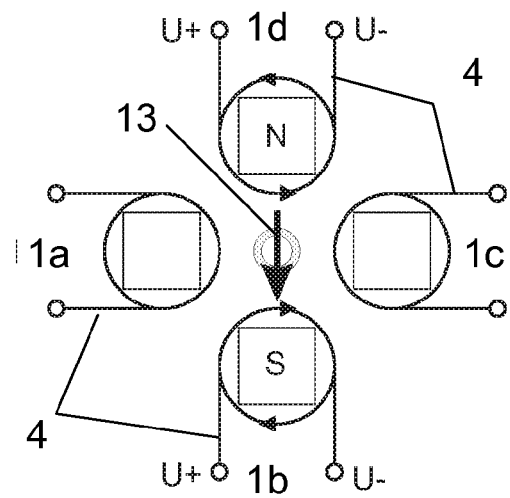
FIGS. 3a, b and c show a sequence of illustrations of the spatial position change of the magnetic field orientation by an electromagnet arrangement.

FIG. 1 shows an EMUS transducer system in a perspective oblique view, which has more than four individual magnetization bodies 1a, 1b, 1c and 1d, which bear in a flush manner against the test specimen surface of a test specimen 2 with their ends free at the end face in each case. The magnetization bodies 1a, 1b, 1c and 1d are in a longitudinal, preferably cuboidal or bar-like manner and furthermore, integrally connected to a cross yoke 1x at their end regions facing away from the test specimen 2 in each case. The magnetization bodies 1a, 1b, 1c and 1d, also in the form of the cross yoke 1x, are manufactured from a ferromagnetic material and constitute an electromagnet arrangement in connection with magnetization coils 4 which are in each case arranged around the individual magnetization bodies 1a-1d. Taking account of a voltage unit supplying the individual magnetization coils 4 with electrical energy has been dispensed with for reasons of better clarity of illustration.

In projection onto the test specimen surface centrally below the cross yoke arrangement 1x, a HF coil system 3 is located on the test specimen surface, providing a high-frequency which is able to modulate the magnetic field prevailing within the test specimen 2, to provide linearly polarized ultrasound transverse waves within the test specimen 2.

Figure 3B:
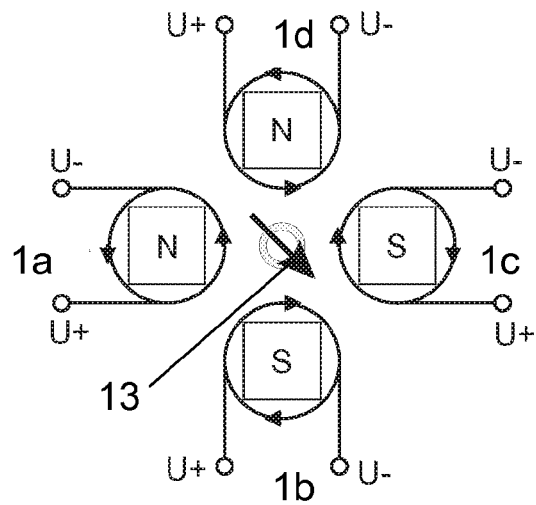
Figure 3C:
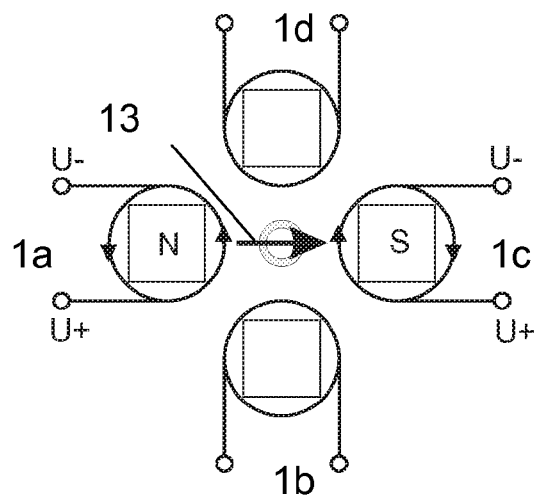

To illustrate the change of the spatial orientation of the magnetic field prevailing within the test specimen 2, reference is made to the image sequence illustration in the FIGS. 3a-3c, in which the four magnetization bodies 1a-1d are illustrated in each case projecting onto the test specimen surface 4 which surround them in each case. In the image sequence illustration according to FIG. 3a, it is assumed that the magnetization coils of the magnetization bodies 1a and 1c are switched in a currentless manner, so that no magnetic field prevails between these two magnetization bodies 1a and 1c. The magnetization coils 4 are activated with respect to the magnetization bodies 1b and 1d so that the magnetization body 1b forms a magnetic south pole on the test specimen surface and also the magnetization body 1d forms a magnetic north pole. Thus, there results a magnetic field 31 orientated parallel to the test specimen surface having magnetic field lines orientated from north to south, that is to say from top to bottom in the case illustrated according to FIG. 3a.

If, in addition to the activated magnetic coils on the magnetization bodies 1b and 1d, the magnetization bodies 1a and 1c are also activated, as is illustrated in FIG. 3b. Then two magnetic fields are overlayed to form a resulting magnetic field 13 in the central region of all four magnetization bodies 1a-1d in the manner indicated in FIG. 3b. In this case, a magnetic field 13 is spatially rotated through 45° compared to the image sequence according to FIG. 3a is set.

If, as in the case of the sequence according to FIG. 3c, the magnetization coils of the magnetization bodies 1b and 1d are switched currentlessly, then the magnetic field between the magnetization bodies 1a and 1c prevails exclusively, that is to say the magnetic field 13 orientated parallel to the test specimen surface then points from left to right. When the sequence of images of FIGS. 3a to 3c are viewed together, the orientation of the magnetic field 13 has therefore been rotated through exactly 90°, without spatially moving the magnetization bodies 1a, 1b, 1c, 1d in the process.

Figure 4:
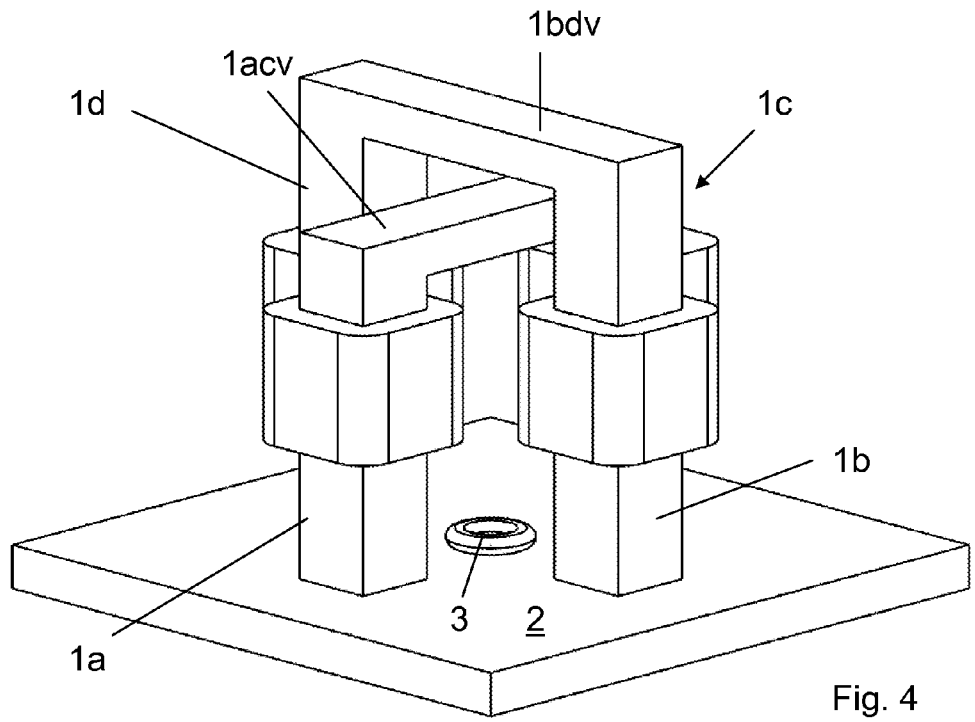
FIG. 4 shows an EMUS transducer system in the form of an electromagnet arrangement with separately constructed magnetization body pairs in crossed state; and also

FIG. 4 shows a further embodiment, which like the exemplary embodiment illustrated in FIG. 1, has four magnetization bodies 1a to 1d, which are not connected to one another via an integral cross yoke. However, in each case pairs are connected magnetically via magnetically active connecting yokes 1acv, 1bsv. To realize the crossed state, like those in FIG. 1, the magnetization bodies 1b and 1d are constructed in a longer manner compared to the magnetisation bodies 1a and 1c, so that the individual magnetically active connecting yokes 1acv, 1bdv cross over in a regular manner. The mechanism of action is identical to that which has been explained with reference to the image sequence illustration according to FIGS. 3a to 3c.

Figure 5:
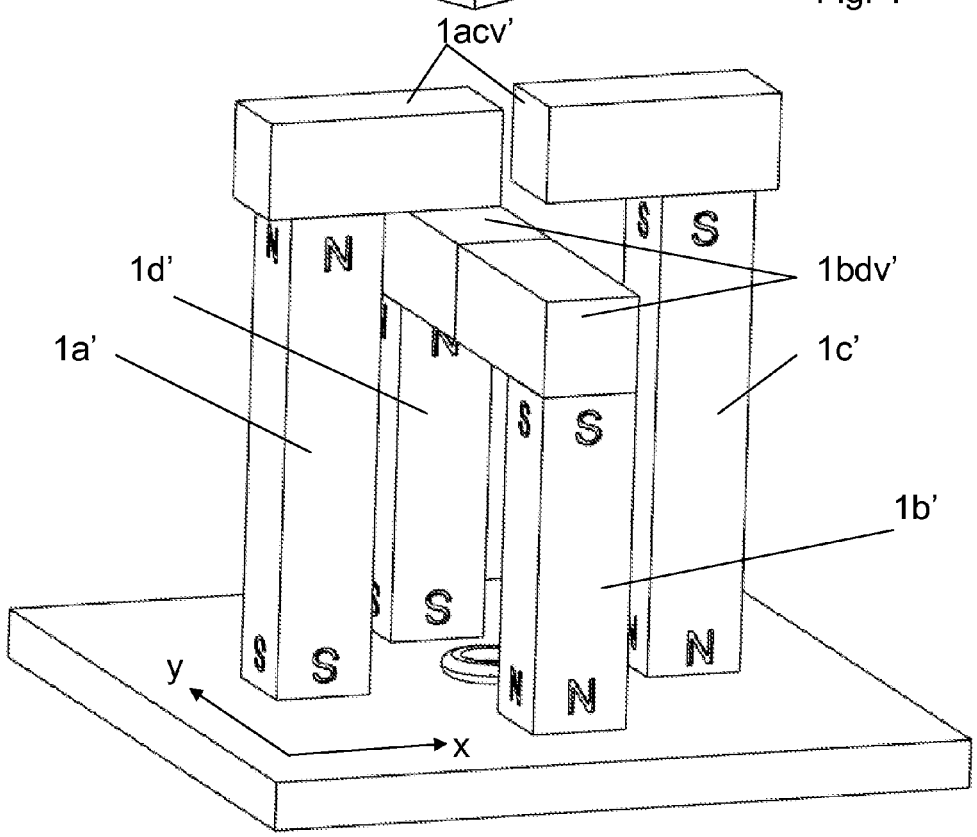
FIG. 5 shows an EMUS transducer system in the form of a permanent magnet arrangement.

In FIG. 5, an embodiment for an EMUS transducer system with a magnetisation unit is shown, which consists exclusively of permanent magnets 1a', 1b', 1c' and 1d'. The magnetic poling of the permanent magnets 1a' to 1d' constructed as bar magnets result on the basis of the designations for N=north pole and S=south pole contained in FIG. 5. A first magnetic field orientated parallel to the test specimen surface within the test specimen 2 is generated by the permanent magnets 1a' and 1c' in the x direction and a second magnetic field orientated parallel to the test specimen surface is generated by the permanent magnets 1b' and 1d' in the y direction. The x and y directions are orientated orthogonally to one another.

In addition, the permanent magnet pairs 1a'/1c' and also 1b'/1d' are in each case connected to one another via separately constructed magnetically active connecting yokes 1acv' and 1bdv'.

In order to be able to pivot the direction of the magnetic field at the location of the HF coil system 3 within the test specimen 2 in a controlled manner, it is valid to vary the magnetic flux through the respectively separately constructed connecting yokes 1$acv'$ and 1$bdv'$. This is achieved in that each individual part of the connecting yokes 1$acv'$ and 1$bdv'$ are spatially movably mounted via an actuator which is not illustrated further. If both parts of the respective connecting yoke are in direct contact, as is the case in FIG. 5 for the permanent magnets 1$b'$ and 1$d'$ illustrated, then the magnetic flux in this connecting yoke 1$bdv'$ considered is maximal. Consequently, the magnetic flux which is introduced by means of the permanent magnets 1$b'$ and 1$d'$ into the test specimen 2 is also maximal. If, however, there is an air gap between the two parts of the connecting yoke, as is the case in FIG. 5 for the permanent magnets 1$a'$ and 1$c'$, then the magnetic flux is reduced as a function of the gap width. In the case of FIG. 5, the test specimen 2 is primarily magnetized by the permanent magnets 1$b$/1$d$ short-circuited by means of the connecting yoke 1$bdv'$. This connecting yoke 1$bdv'$ therefore also specifies the direction of the magnetic field in the test body at the location of the HF coil system. If, by contrast, the air gap is closed in all of the connecting yokes, then the magnetic fields of both yokes or both permanent magnet pairs 1$a''$/1$c'$ and 1$b'$/1$d'$ are overlaid, so that a magnetic field direction of 45° is set, comparably to the image sequence illustration in FIG. 3$b$.

With a suitable actuator, with which it is possible to vary the position of the parts of the connecting yokes 1$acv'$ and 1$bdv'$ in the manner described previously, direction and field strength of the resulting magnetic field within the test specimen 2 at the location of the HF coil system 3 can be changed with mechanical means exclusively.

As already mentioned previously, it is fundamentally possible to choose the number of magnetization bodies involved arbitrarily for producing a resulting magnetic field within the test specimen 2, that is to say at least n=3 magnetization bodies, preferably however an even number n.

A series of advantages is connected with the EMUS transducer system according to the invention. The EMUS transducer system does not have to be mechanically rotated with respect to the test specimen in order to change the polarization direction of the transverse wave. The position of the EMUS transducer system can be maintained exactly during the rotation of the polarisation direction, as the transducer itself is not moved.

The transducer principle can be used for automatic test systems without coupling means, so that it is also available for applications at high temperatures.

The main directions of anisotropic test specimens do not need to be known before the test. The EMUS transducer system can be placed and positioned onto an otherwise unknown test body. Nonetheless, it is possible to discover the main directions by stationary rotation of the polarization direction. Fundamentally, any polarization directions of the linearly polarized transverse waves can be set.

Further, it is possible by measuring the speed of sound as a function of polarization direction to detect textures and/or inner stresses in accordance with thickness and direction. For fault checking, the possible direction of a crack can be detected fully automatically by the rotation, in accordance with the invention, of the polarization direction. Further, for example, in the case of strongly anisotropic materials, the optimum polarization direction for the test task can be discovered without an elaborate mechanical rotation of the entire probe.

REFERENCE LIST

1 Magnetization unit
1$a,b,c,d$ Magnetization body
1$a',b',c',d'$ Permanent magnets
1$x$ Cross yoke
1$acv$, 1$bdv$ Magnetically active connecting yoke
1$acv'$, 1$bdv'$ Separated connecting yoke
13 Magnetic field
2 Probe
3 HF coil system
4 Magnetization coils

The invention claimed is:

1. An EMUS transducer system for producing linearly polarized transverse waves having a variably predeterminable polarization direction within a test specimen containing at least ferromagnetic material portions and having a test specimen surface, comprising:
    a magnetization unit for producing a magnetic field orientated parallel to the test specimen surface within the test specimen, at least one HF coil on the test specimen surface for producing or detecting a HF field combined with the magnetic field orientated parallel to the test specimen surface within the test specimen, the magnetization unit including at least three magnetization bodies spatially separated from one another and which are positionable on the test specimen surface for introducing a magnetic field having a predeterminable magnetic flux into the test specimen; and
    means for changing the magnetic flux emanating from at least one of magnetization bodies to vary a spatial direction of the magnetic field relative to the test specimen surface within the test specimen.

2. An EMUS transducer system according to claim 1, wherein:
    the magnetization bodies include an accessible surface at an end face and a region opposite the accessible surface for placement onto the test specimen surface which is connectable via at least one magnetically active yoke to at least one other magnetization body.

3. An EMUS transducer system according to claim 1, wherein:
    the magnetization unit comprises an electromagnet;
    the means for changing the magnetic flux comprises electrical coils with at least one electrical coil being attached to only one magnetization body; and
    the electrical coils are connected to a controllable direct or alternating current source.

4. An EMUS transducer system according to claim 1, wherein:
    the magnetization bodies each comprise a permanent magnet; and
    the means for changing the magnetic flux comprises at least one magnetic flux conducting piece with each piece having a spatial location which can be changed relative to the at least one magnetization body.

5. An EMUS transducer system according to claim 4, wherein:
    the magnetic flux conducting pieces of at least two magnetization bodies are parts of a magnetically active connecting yoke; and further comprising
    a controllable kinematic unit for changing a spatial position of at least one magnetic flux conducting piece.

6. An EMUS transducer system according to claim 1, wherein:
    the magnetization unit comprises an electromagnet and a permanent magnet; and the means for changing the magnetic flux comprises electrical coils of the electromagnet with at least one electrical coil being attached to only one magnetization body;

the at least one electrical coil is connected to a controllable direct or alternating current source; and the means for changing the magnetic flux comprises at least one magnetic flux conducting piece of the permanent magnet and has a spatial location which can be changed relative to the at least one magnetization body.

7. An EMUS transducer system according to claim 1, wherein:

at least two magnetization bodies are connectable via a magnetically active connecting yoke and form a magnetization body pair; and at least two magnetization body pairs are constructed with magnetically active connecting yokes and the at least two magnetization body pairs cross or project onto the test specimen surface.

8. A method for producing ultrasound waves comprising:

producing linearly polarized transverse waves by electromagnetic creation of ultrasound which have a variable polarization direction within a test specimen containing at least ferromagnetic material portions with a magnetic field within the test specimen being produced which is orientated parallel to a surface of the test specimen and an electromagnetic field is produced by a coil, is parallel to the test specimen surface and is modulated; and wherein at least two magnetic fields orientated parallel to the test specimen surface are produced within the test specimen and form at an angle with the test specimen which does not equal 0'; and changing the magnetic flux of at least one of the two magnetic fields to provide a uniform magnetic field orientated parallel to the test specimen surface.

9. A method according to claim 8, comprising:

producing at least two magnetic fields orientated parallel to the test specimen surface within the test specimen with an electromagnet; and changing the magnetic flux of at least one magnetic field by an electrical supply voltage of the electromagnet which produces the at least one magnetic field.

10. A method according to claim 8, comprising:

producing at least two magnetic fields orientated parallel to the test specimen surface within the test specimen by a permanent magnet; and changing the magnetic flux of the at least one magnetic field is performed by spatial variation of at least one permanent magnet or a magnetic flux conducting piece.

11. A method according to claim 8, comprising:

producing at least one magnetic field orientated parallel to the test specimen surface with a permanent magnet and at least one further magnetic field orientated parallel to the test specimen surface within the test specimen by an electromagnet; and wherein changing the magnetic flux of the at least one magnetic field produced by the permanent magnet is performed by spatial variation of at least one permanent magnet or a magnetic flux conducting piece and an electrical supply voltage of the electromagnet produces the at least one magnetic field.

12. An EMUS transducer according to claim 1, comprising:

four magnetization bodies spatially separated from one another.

13. A method in accordance with claim 8 wherein:

the angle equals 90°.

* * * * *